United States Patent [19]

Westermark et al.

[11] Patent Number: 5,112,945
[45] Date of Patent: May 12, 1992

[54] PREPARATION OF ISLET AMYLOID POLYPEPTIDES (IAPP) AND ANTIBODIES TO IAPP

[75] Inventors: Per Westermark, Dalinge, Sweden; Kenneth H. Johnson, Minneapolis, Minn.

[73] Assignee: Regents of the University of Minnesota, Minneapolis, Minn.

[21] Appl. No.: 658,442

[22] Filed: Feb. 21, 1991

Related U.S. Application Data

[63] Continuation of Ser. No. 105,267, Oct. 7, 1987, abandoned.

[30] Foreign Application Priority Data

Oct. 8, 1986 [SE] Sweden .................................. 8604270

[51] Int. Cl.5 .......................... C07K 7/40; C07K 7/10
[52] U.S. Cl. .................................... 530/324; 530/303; 530/327; 530/845
[58] Field of Search ............... 530/300, 324, 327, 303, 530/845

[56] References Cited

PUBLICATIONS

Cooper, G. J. S. et al. PNAS 84:8628, Dec. 1987, "Purification and characterization . . .".
Mosselman, S. et al. FEBS Lett. 247(1):154–158 Apr. 1989 "The complete islet amyloid . . .".
Marglin, A. and R. B. Merrifield Chemical Synthesis of Peptides, 1970.
Westermark, P. et al. 1983, Diabetologia 24:342–346, Islet Amyloaid in Type 2 . . . .
Fang, T. Y. et al. 1986, Pancreas 1(4):293–300, Immunohistochemical study . . . (see abstract).
C. Betsholtz et al., Exper. Cell Res., 183, 484 (1989).
T. D. O'Brien, Am. J. Pathol., 119, 430 (1985).
K. H. Johnson et al., Vet. Pathol., 22, 463 (1985).
K. Higuchi et al., Lab. Invest., 48, 231 (1983).
C. Betsholtz et al., Diabetes, 39, 118 (1990).

Primary Examiner—Christine M. Nucker
Assistant Examiner—T. Cunningham
Attorney, Agent, or Firm—Merchant, Gould, Smith, Edell, Welter & Schmidt

[57] ABSTRACT

Subunits of the full length 37 amino acid residue human Islet Amyloid Polypeptide, and feline Islet Amyloid Polypeptide essentially free of unpolymerized amyloid are provided. Islet Amyloid Polypeptide (IAPP) may be isolated and purified from amyloid fibrils using depolymerizing agent and chromatographic techniques. The sequences of the purified Islet Amyloid Polypeptides have been determined Purified Islet Amyloid Polypeptides are suitable for induction of anti-IAPP antibodies.

4 Claims, 1 Drawing Sheet

PREPARATION OF ISLET AMYLOID POLYPEPTIDES (IAPP) AND ANTIBODIES TO IAPP

This invention was made with the support of NIH Grant No. R01-DK 36734.

This application is a file wrapper continuation of Ser. No. 07/105,267, filed Oct. 7, 1987, now abandoned.

FIELD OF THE INVENTION

The invention is concerned with a newly characterized polypeptide and with antibodies directed against that polypeptide. Potentially the polypeptide, fragments thereof having the biological activity corresponding to that of the polypeptide, and proteins containing the amino acid sequence of the polypeptide or of the said fragments thereof can be employed for therapeutic purposes and for diagnosis of diseases related to the biological function of the polypeptide. Since the polypeptide has been characterized for the first time in amyloid fibrils from a patient having an insulin-producing pancreatic tumor (insulinoma) this polypeptide will henceforth be called "IAPP", this being an abbreviation of "insulinoma amyloid polypeptide" or "islet amyloid polypeptide". During the priority year IAPP has also been called diabetes-associated peptide (=DAP) (34). Unless otherwise stated, the term IAPP comprises the polypeptide as such, fragments thereof having a corresponding biological activity, soluble proteins containing the amino acid sequence of the polypeptide, and furthermore also analogous proteins, polypeptides and fragments from mammals other than humans. The term "preparation" is used for the purpose of clearly stating that the preparations of the invention have been specifically worked up in respect to IAPP or its homologous antibodies. The invention thus relates to in vitro preparations and not to the in vivo occurrence of the proteins.

BACKGROUND OF THE INVENTION

Non-insulin-dependent diabetes mellitus (NIDDM) is characterized by an impaired insulin response to elevated glucose levels which, in contrast to insulin-dependent diabetes mellitus (IDDM), is not primarily due to loss of beta-cells even though the total beta-cell mass is moderately diminished in NIDDM (1, 2). Despite the apparent multifactorial nature of the pathogenesis of NIDDM, and regardless of whether beta-cell dysfunction is primary or secondary, the most substantial and uniform morphological aspect of this disease with respect to the islets of Langerhans is the deposition of amyloid. These deposits (islet amyloid=IA) which are exclusively limited to the islets of Langerhans occur in more than 90% of NIDDM patients and in over 65% of adult diabetic cats (3–5). IA occurs also in old persons and in aged cats but less frequently and to a lesser extent. In contrast to the NIDDM cases, no IA deposits have been found in association with IDDM.

The significance of IA has been a matter of discussion ever since the first description of the phenomenon in 1900 (6). Although isolated and purified IA might potentially have served as a useful marker for detection of an islet cell dysfunction associated with the development of NIDDM it has not been possible heretofore to achieve a chemical analysis of IA. The principal obstacle to chemical characterization and to amino acid sequencing of the subunits has resided in the difficulty encountered in effectuating solubilization (depolymerization) of the IA fibrils (7). This difficulty of solubilizing IA, which has contributed to the elusive nature of this material, constitutes a direct contrast to the two major systemic forms of amyloid (i.e. AA or secondary amyloid and AL or primary amyloid) both of which can be depolymerized with 6M guanidine hydrochloride after suspension in distilled water. These properties of systemic forms of amyloid have permitted purification and direct chemical analysis of the amyloid fibril protein subunits.

In all instances, amyloid is a pathological deposit of polymerized subunits which form beta-pleated sheet fibrils (8). Many different types of amyloid exist and these may occur systemically or be localized to individual tissues (9). Each type is characterized by its protein subunits, and up to now seven different proteins have been shown to be capable of forming amyloid fibrils in vivo (10–17).

Amyloid in polypeptide hormone producing tissues has been proposed to consist of corresponding hormones (18, 19). This is best supported for human medullary carcinoma of the thyroid where the subunits of the amyloid fibrils formed have been shown, after amino acid sequencing, to consist of procalcitonin (13). Since amyloid deposits are common in insulin producing tumors (19) and because there is a close relationship between the amyloid fibrils in islet beta-cells and insulin-producing tumors, it was believed previously that the amyloid in these locations is derived from insulin or its precursor. The invention is based on our discovery that IA mainly contains a hitherto unknown polypeptide, now named IAPP.

In an International Type Search Report compiled by the Swedish Patent Office during the priority year, the references 26–31 have been cited. References 26–28 deals with unsuccessful attempts to isolate and characterize the major component of islet amyloid. Reference 29 describes a systemic form of amyloid that is completely distinct from islet amyloid. See for instance the preceding paragraph. References 30 and 31 have been cited as defining the general state of the art and have not been considered to be of any particular relevance.

SUMMARY OF THE INVENTION

Among the principal aspects of the invention are kits of material containing at least one protein preparation (=polypeptide preparation) selected from amount IAPP preparations and anti-IAPP antibody preparations, and the use of said kits for the formation of complexes and anti-IAPP antibodies. Among subordinate aspects of the invention are the protein preparations as such, and methods of determining IAPP with the aid of an antibody preparation of the invention. An aspect to be mentioned also is the potentially very important therapeutical use of IAPP preparations for positively influencing IAPP-regulated biological functions.

DETAILED DESCRIPTION OF THE INVENTION

The IAPP preparations of the invention are characterized by containing IAPP while at the same time being substantially free from the amyloid form. If the IAPP derives from a human insulinoma its amino acid sequence is the one set forth in Table 2, especially in respect of the amino acid residues in positions 3–35 or 8–33 (see comments to the Tables). The same sequence applies to IAPP isolated from IA taken from NIDDM patients. As compared with human IAPP the IAPP deriving from other mammals shows minor differences in the amino acid sequence. The term "IAPP preparation according to the invention" comprises also various derivatives of IAPP. Thus IAPP according to the invention can be provided with some of the analytically detectable groups that are well known in immunochemical assay methods; such as e.g. radioactive, enzymatically active, fluorogenic, chemiluminogenic, biotinyl etc. groups. Also, the IAPP may be attached to any of the various different types of carrier molecules that are well known in immunochemical and immunosorbent contexts. In the IAPP preparations according to the invention, the IAPP is usually the principal constituent, i.e. amounts to $>50\%$, as for instance $<90\%$ (w/w) of the proteins from the source of raw material.

Preparations enriched in IAPP can be produced in that at first polymerized IAPP, i.e. IA, is isolated in a manner known per se from tissues containing such IAPP as e.g. from insulinomas or from islets of Langerhans of NIDDM patients, whereupon the IA thus obtained is depolymerized under conditions that will not appreciably hydrolyze the subunits. As a suitable depolymerizing agent may be mentioned concentrated formic acid. Temperatures may be within the range of 0°–50° C.; but note here that it is always necessary to pay due regard also to all the other working conditions, as e.g. the depolymerizing agent chosen. IAPP may potentially be produced also from cell cultures. With the aid of recombinant DNA techniques synthetic DNA and cDNA coding for IAPP may be introduced into microorganisms which will then be made to produce the peptide. Now that the amino acid sequence of IAPP has become known it is also possible to manufacture IAPP synthetically, in a manner such as is known per se for peptide syntheses. In order to be converted to a pure form the IAPP must be worked up (extracted) from the reaction mixtures (including culture media) which are obtained in accordance with any one of the aforesaid methods. For this purpose a large number of various different biochemical separation procedures may be employed, such as electrophoresis, e.g. isoelectric focusing, centrifugation and/or liquid chromatography. Among these latter may be mentioned high pressure liquid chromatography (HPLC), and gel, affinity and ion exchange chromatography. In particular HPLC will lend itself to producing a high degree of purity of IAPP.

As regards the anti-IAPP antibody preparations of the invention, these have to be specific to IAPP and should not react immunochemically with other substances in a manner that would interfere disturbingly with a given use. The anti-IAPP antibody preparation of the invention has no significant reaction with e.g. insulin (native form, A- or B-chain thereof) and calcitonin gene related peptides (CGRPs). Anti-IAPP antibodies may be produced in a manner as is common practice for antibodies, by means of immunizing a suitable animal (e.g. rabbit, rat, mouse etc.) with an IAPP-immunogen, followed by working up the resultant antibodies to obtain a desired purity and form thereof (derivatives, fragments etc.). The production of the anti-IAPP antibodies may by the known monoclonal technique. The anti-IAPP antibodies of the antibody preparation may thus be present in the form of an antiserum or may be affinity purified, derivatized (e.g. covalently bound to one of the above-mentioned types of analytically detectable groups, or chemically or physically bound to a phase which is insoluble in aqueous media=a so-called "solid" phase) or fragmentized into various anti-IAPP antibody active components, like Fab, Fab' or F(ab')$_2$.

In order to obtain a high yield and/or quality in the production of an anti-IAPP antibody preparation, the antigen used in the immunization protocol or in the selection of the appropriate antibodies in a polyclonal antibody response may be critical. With respect to antigens comprising only short sequences of IAPP, the sequence of positions 1–6 should be avoided. In order to make an efficient selection in a polyclonal antibody response, different combinations of antigens can be used. For instance in monoclonal techniques one can start by selecting IAPP-reacting clones and then in a secondary selection discard those reacting with CGRPs.

In general terms the production of an antibody preparation according to the invention (monoclonal as well as polyclonal) is performed in that cells potentially capable of producing antibodies that possess a specificity in accordance with the invention are caused to excrete said antibodies, whereupon the antibodies thus excreted are isolated and purified so as to remove those antibodies that do not fulfill the specificity requirements.

Some variant forms of the invention may utilize antibodies or IAPP in a so-called solid-phase-bound form. Binding proteins to solid phases and using them in e.g. immunological assay methods is prior art technique (20). Examples of solid phases are particulate matrices which are hydrophilic and swellable to form gels but insoluble in water. In many cases such matrices contain OH or NH$_2$ groups (for example polyamides, polysaccharides, poly(hydroxyalkylacrylates) and corresponding methacrylates etc.). The antibody or IAPP of the invention may be covalently or adsorptively bound to a water-insoluble matrix.

The protein preparations of the invention may be used for forming, in vivo as well as in vitro, so-called ligand-receptor complexes cohering due to biospecific affinity. The ligand-receptor concept is well known in patent contexts and comprises such pairs of substances like enzyme-substrate; hormone-receptor for that hormone; antigen(hapten)-antibody etc. In the present specification and claims, the term "ligand" always refers to IAPP, and the term "receptor" always refers to antibody or the counterpart with which IAPP has to cooperate in vivo in order that a biological effect be obtained in vertebrates, preferably mammals, such as man.

The ligand-receptor complexes of the invention may be formed (1) for the purpose of obtaining a biological response in vivo,
(2) in vitro as one of the steps of an immunosorbent process, or
(3) in vitro as one of the steps of an immunochemical assay method.

For forming the complexes in vivo, the IAPP in an amount effective for the purpose contemplated and incorporated in a suitable sterile formulation is administered to the animal in a site on the animal that is suitable for the purpose. As vehicles may be mentioned sterile aqueous media such as physiological saline. If a therapeutical treatment is to be carried out a therapeutically active (=effective) amount is administered; and in case an immunization is to be carried out the amount of IAPP administered is one that is immunogenically active (=effective), the IAPP being preferably conjugated to an immunogenic carrier.

For forming the complexes in vitro a preparation according to the invention is mixed (administered) with (to) a sample containing an immunological counterpart to the agent present in said preparation, under conditions such that the immune complex can be formed. This may be done in various ways. If several different preparations according to the invention are employed the exact order is determined by the objects for which the immune complex is to be used. The conditions are those commonly employed for immune reactions, i.e. aqueous media buffered to a pH which will normally be within the range of from pH 3.5 to 9.0, preferably 5.0-8.6. Temperatures are usually maintained in the range or from $+4°$ to $+40°$ C. Additions may be made of buffers and detergents that will not interfere with the immune reaction or its result.

That aspect of the invention which comprises immunosorbent purification of IAPP involves the binding of anti-IAPP antibodies (e.g. solid-phase-bound) to IAPP, the thus resultant immune complex then being separated from the reaction mixture, whereupon in a manner as known per se in connection with immunosorbent purification procedures IAPP can be released from the complex and, if required, be subjected to further work-up treatment. In cases where anti-IAPP antibodies are to be purified, IAPP may be employed in an analogous manner. Temperature and pH are selected as set forth in the preceding paragraph.

The immunochemical assay method of the invention comprises subjecting antibodies directed against IAPP to reaction with the IAPP present in a sample to thus form an (IAPP-anti-IAPP) immune complex, the formation and amount of which are measures—qualitative and quantitative, respectively—of the IAPP presence in the sample. For facilitating detection and quantification a practice frequently relied on is to add further immune reactants or other reactants capable of biospecifically reacting with constituents of the complex. They may be anti-antibodies provided with analytically detectable groups.

Several different immunochemical assay methods are available; the artisan on the basis of his given analyte will decide in each case which method is best for the purpose. This applies also to IAPP. Among various existent methods may be mentioned: competitive (inhibition) and non-competitive methods, precipitation methods, heterogeneous and homogeneous methods, various methods named according to the analytically detectable group employed, immunoelectrophoresis, particle agglutination, immunodiffusion and immunohistochemical methods employing labeled antibodies.

The technical effect of the protein preparations according to this invention is demonstrated in the experimental portion, showing that IAPP preparations may be used for making anti-IAPP antibody preparations which in turn may be employed in histochemical assays for IAPP and IA in biological tissue of e.g. NIDDM patients.

The individual aspects of the invention are defined more specifically in the attached claims which form an integral part of the specification.

The invention will now be illustrated by means of the underlying scientific work forming the basis for this invention.

EXAMPLES

Material and Methods

Figure 1:
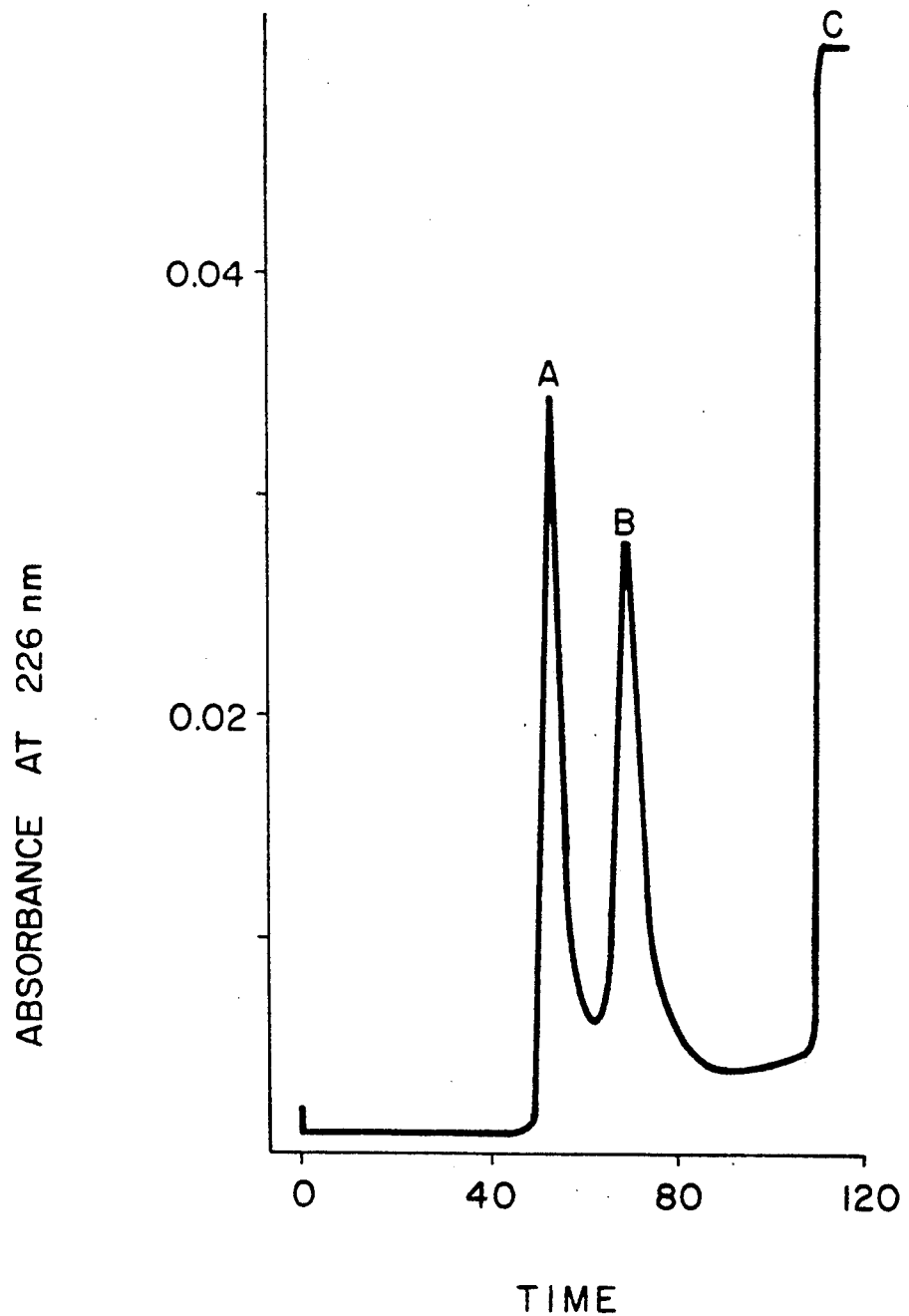
FIG. 1 is an elution curve obtained during the purification of subunits of IA.

A. Purification of Subunits of IA (Isolation of IAPP)

Amyloid fibrils were isolated from an insulin-producing tumor taken from a 48-year-old man. 2 g of tumor tissue, of which 50% consisted of amyloid, was homogenized repeatedly in normal saline followed by washing in distilled water until all of the soluble protein had been removed. The resultant pellet was lyophilized, defatted with chloroform-methanol (2:1) and treated with 6M guanidine-HCl, 0.1M Tris HCl, pH 8.0, 0.1M EDTA and 0.1M dithiothreitol. After undissolved material has been centrifuged and washed in distilled water smears stained with Congo red and examined in polarized light showed that the residual material consisted mainly of amyloid. The pellet was lyophilized and treated with formic acid over night at room temperature, involving dissolution of most of the material. After centrifugation the supernatant was subjected to evaporation. 1 mg of the evaporation residue was boiled quickly in 0.5 ml of 1% (w/v) sodium lauryl sulfate (=SDS) solution containing 0.05M sodium phosphate buffer, pH 7.5. Then 0.2 ml of the reaction mixture was subjected to HPLC on a TSK G2000SW ($7.5 \times 600$ mm) column (apparatus and column were from LKB, Bromma, Sweden). Elution was performed with the phosphate-buffered SDS solution and at a flow rate of 0.2 ml/min. The elution curve was taken up at 226 nm with the aid of an LKB 2158 SD wavelength detector equipped with an LKB 2152 integrator (LKB, Bromma, Sweden). The curve is shown as FIG. 1. The column used has the capability of separating proteins of molecular weight 500–60,000 dalton.

The same procedure was followed in isolating and purifying the subunits of amyloid from cat Langerhans islets and from an NIDDM patient.

B. Analysis of IAPP Amino Acid Sequence

Fractions corresponding to the retarded protein peak (B) were precipitated with 9 volumes of ethanol at $-20°$ C. The precipitate was dried, dissolved in 50% trifluoroacetic acid, and applied to a gas phase sequenator (Applied Biosystems, U.S.A.). The amino acid residues were determined as PTH amino acids directly by HPLC. The percent composition of amino acids was determined after acid hydrolysis for 24 hours.

C. Immunohistochemistry. IAPP Derivative and Its Use. Production and Use of Anti-IAPP Antibody Preparation and Its Use An undecapeptide corresponding to positions 7–17 of the human insulinoma IAPP and with an extra N-terminal cystine residue was synthesized and conjugated with keyhole limpet hemocyanine by Cambridge Research Biochemicals Ltd., Harston, England. The conjugated peptide, dissolved in 0.1M NaOH and admixed with Freund's complete adjuvant, was injected subcutaneously into guinea pigs. Immunization was then continued by means of one injection per week, although now with the immunogen in Freund's incomplete adjuvant. Serum was harvested a week after the fourth injection. Human and cat pancreases shown by Congo red staining to have large amounts of IA, and surgical specimens were fixed in 4% formalin, embedded in paraffin and sectioned. Deparaffinized sections were studied by the peroxidase-antiperoxidase method (22) using primary anti-IAPP antiserum in dilutions of 1:50–1:800. Controls were guinea pig serum and primary antiserum adsorbed with the synthetic peptide (10 mg/ml).

By the same technique the presence of IAPP in a dog, mouse, rat, guinea pig, hamster and monkey have been demonstrated. The technique has also been applied for an anti-CGRP antiserum demonstrating a distinct staining pattern for the latter compared to that of an anti-IAPP antibody preparation. This indicates that the two antibody preparations have different specificities.

D. Synthesis of Human IAPP$_{1-37}$

Human IAPP: lys-cys-asn-thr-ala-thr-cys-ala-thr-gln-arg-leu-ala-asn-phe-leu-val-his-ser-ser-asn-asn-phe-gly-ala-ile-leu-ser-ser-thr-asn-val-gly-ser-asn-thr-tyr In an attempt to synthesize the complete sequence of human IAPP the procedure of Mahoney, W. C. (36) has been followed.

The polypeptide is syntesized using a Beckman Model 990B peptide synthesizer. All amino acid residues are protected at the α-amino position with the tert.-butyloxycarbonyl (Boc) group (37). All amino acids were purchased from Peninsula Laboratories. The synthetic peptides are deprotected and simultaneously removed from the resin by treatment with anhydrous HF, using the SN$_2$ approach of Tam et al (32).

Peptide purification was accomplished by reversed-phase high-performance liquid chromatography using volatile buffers as described by Mahoney and Hermodson (39), followed by quantification by amino acid analysis. A small amount of each peptide (0.5 mg) was modified at the carboxyl terminus by suspending the peptide in dry methanol and concentrated HCl at ambient temperature for 24 h. The resulting peptide methyl ester derivatives were purified by reversed-phase high-performance liquid chromatography, as described above.

Peptide sequencing was accomplished by automated Edman degradation (40–42) using a Beckman Model 890DS sequencer, operated using 0.1M Quadrol buffer and a modification of Beckman peptide program 345801. Prior to addition to a sample to the cup 1.8 mg of Polybrene, dissolved in 50% acetic acid, was applied to the sequencer cup, dried under vacuum, and subjected to three complete cycles of Edman degradation. Subsequently, the sample as applied to the cup and degraded under the direction of the same program. Samples were prepared for the analysis and identified by high-performance liquid chromatography as previously described (41, 42).

Amino acid analyses were performed using a Beckman Model 6300 amino acid analyzer. Spectra were taken using a LKB 4050 Ultraspec which was interfaced to a Vacs 11-750 computer. Spectra were taken following a 10-min incubation at room temperature upon all reagent additions.

Results

Repeated homogenizations of insulinoma and pancreatic tissue in normal saline followed by guanidine HCl extraction resulted in both cases in microscopically nearly pure amyloid. The amyloid obtained, which was insoluble in guanidine-HCl, was dissolved in concentrated formic acid. Lyophilized depolymerized amyloid was soluble in SDS.

Gel chromatography (HPLC) of depolymerized pancreatic IA from humans (insulinoma) as well as cats gave elution profiles having substantially just one single retarded protein peak. (FIG. Peak B.) Fractions corresponding to this peak were subjected to automated gas phase sequencing of amino acids. One amino acid was released in each step. The amino acid sequences of the two polypeptides, isolated from insulinoma and from cat Langerhans islets respectively, are shown in Table 1. The insulinoma polypeptide was run for 40 cycles of amino acid sequencing, but no amino acid residues could be demonstrated after 37 cycles. The percent composition of amino acids as calculated on the basis of the amino acid sequence is in complete agreement with the composition that can be calculated after acid hydrolysis (Table 1). No amino acid residues were found in positions 2 and 36 of the insulinoma polypeptide. Since according to amino acid analysis (Table 2 col. A) the polypeptide contains cystine (cysteine) and since human CGRP (with which there is a certain degree of partial identity) has cystine bridging position 2 and 7, it is highly probable that in the pancreatic tumor polypeptide studied position 2 is represented by cysteine. Amino acid sequencing of human IAPP was initiated but was discontinued after 18 cycles because by then no difference from insulinoma IAPP had shown up. The result, taken together with the similarity in the amino acid composition of the peptides, reveals them to be identical.

Based on amino acid sequence, the molecular weight of the human pancreatic tumor peptide is about 3,800–3,900 daltons.

Computer-based comparison with the amino acid sequences of known proteins, in accordance with the "Search" program (Protein Identification Resource, Release 7, Biomedical Research Foundation, Georgetown University Medical Center, Washington, D.C., U.S.A.) shows partial identity with the calcitonin gene related peptide (CGRP) (23, 24), see Table 3. Although the amino acid sequences of the two peptides are similar there are also several distinct differences from which it is clear that they are not identical. There is no resemblance to preproinsulin or calcitonin. The comparison has clearly demonstrated that the amino acid sequence determined by us has not been described for any previously known protein.

The result of N-terminal amino acid sequencing of the cat amyloid peptide is shown in Table 2. For the amino acid residues of position 3–27 the analysis result was conclusive. The sequence thus found is identical with that determined for the human pancreatic polypeptide except for three amino acid substitutions in positions 17, 18 and 23. The incomplete sequence of the cat peptide represents a 44% identity with the corresponding region of human CGRP.

Using the peroxidase-antiperoxidase technique and primary antiserum directed against the synthetic peptide segment (positions 7–17 of the human tumor peptide), intense immune reactivity was demonstrated in beta-cells of Langerhans islets from normal human pancreas, and in both human and cat IA. Pancreatic tissues other than islet tissue remained entirely unstained. Immune reactivity of the islet cells and IA could not be obtained if the primary antiserum was first adsorbed with the synthetic peptide or if the primary antiserum was replaced by normal guinea pig serum.

DISCUSSION

The studies that have been conducive to this invention have been made in the hope that information about the molecular origin and chemical nature of islet-associated amyloid of both humans and cats will provide important insights into the pathogenesis of age-associated diabetes mellitus (DM). IA resembling the human form often occurs in old female cats afflicted with a form of DM resembling NIDDM (25). Preliminary chemical and immunological studies have shown cat IA to have properties very similar to those of human IA.

The immunohistochemical experiments demonstrate an intense immune reactivity in normal human pancreatic islet cells and in both cat and human IA deposits. These results suggest that IAPP is released locally from islet cells.

Human IAPP and cat IAPP are of the same chemical nature, and similarity with other animals in highly probable. The potential biological and pathobiological significance of this previously unidentified neuropeptide-like substance with respect to pancreatic endocrine function and pathogenesis of NIDDM is also interesting, especially in view of the fact that we have also demonstrated the occurrence of amyloid deposits in pancreatic nerves and in ganglia of diabetic cats. These amyloids deposits were shown to have the same histochemical and immunohistochemical properties as IA and were demonstrated in close association with ganglionic beta-cells. The role of IAPP in islets of Langerhans is unknown but is partial identity with CGRP strongly indicates an important regulatory function.

A condition in which IAPP deficiency may conceivably be an important factor is insulin-dependent (juvenile) diabetes mellitus (IDDM). This disease is characterized by a more or less total loss of the insulin-producing beta-cells (1). Since the results hitherto obtained suggest that IAPP is synthesized in beta-cells it seems probable that IDDM also involves IAPP deficiency. Conceivably this deficiency is responsible for some of the changes seen i IDDM, e.g. kidney lesions or retinopathy. In that case IAPP might perhaps be used therapeutically in IAPP deficiency cases.

TABLE 1

Amino acid compositions of IAPP as purified from amyloid produced by human insulinoma (A), by human islets of Langerhans (B), and by feline islets of Langerhans (C). The values set forth are amino acid residues in % per molecule. Values set forth within parentheses are the corresponding values calculated on the basis of the amino acid sequence of IAPP isolated from human insulinoma. Cystine (cysteine) was determined after performic acid oxidation. ND = Not determined.

|     | A        | B     | C    |
|-----|----------|-------|------|
| Asx | 5.5 (6)  | 4.8   | 4.0  |
| Thr | 4.2 (4)  | 3.6   | 2.7  |
| Ser | 5.3 (5)  | 4.2   | 3.0  |
| Glx | 1.9 (1*) | 1.8   | 2.7  |
| Pro | 0.0 (0)  | Trace | 1.6  |
| Gly | 3.4 (3)  | 4.2   | 3.2  |
| Ala | 3.9 (4)  | 4.2   | 3.2  |
| Cys | 1.5 (2)  | ND    | ND   |
| Val | 2.1 (2)  | 2.4   | 2.2  |
| Met | 0.0 (0)  | 0.0   | 0.0  |
| Ile | 1.0 (1)  | 1.2   | 2.0  |
| Leu | 2.9 (3)  | 3.1   | 4.1  |
| Tyr | 0.9 (1)  | 0.9   | 1.3  |
| Phe | 1.7 (2)  | 1.8   | 1.6  |
| His | 0.8 (1)  | 1.2   | 0.6  |
| Lys | 1.1 (1)  | 0.9   | 2.0  |
| Arg | 1.3 (1)  | 1.3   | 1.8  |

Glx = Glutamine or glutamic acid
Asx = Asparagine or aspartic acid

TABLE 2

Complete amino acid sequence of human insulinoma IAPP compared to a part of cat IAPP. *Not yet determined with certainty.

Human IAPP:
Lys—Cys—Asp—Thr—Ala—Thr—Cys—Ala—Thr—Gln—Arg—Leu—Ala—Asn—Phe—Leu—Val—His Cat IAPP:
Lys—Cys—Asn—Thr—Ala—Thr—Cys—Ala—Thr—Gln—Arg—Leu—Ala—Asp—Phe—Leu—Ile—Arg Ser—Ser—Asn—Asn—Phe—Gly—Ala—Ile—Leu—Ser—Ser—Thr—Asp—Val—Gly—Ser—Asn—Thr—Tyr Ser—Ser—Asn—Asn—Leu—Gly—Ala—Ile—Leu

TABLE 3

Amino acid sequence of human insulinoma IAPP compared to the two human CGRPs and to the sequenced part of the IAPP from cat IA. The sequences parts of cat and human IAPP are identical except for positions 17, 18 and 23.

* not yet determined with certainty

Human CGRP1 ( )   A C D T A T C V T H R L A G L L S R S G G M V K S N F V P T N V G S L A F
Human CGRP2 ( )   A C N T A T C V T H R L A G L L S R S G G V V K N N F V P T N V G S L A F Human insulinoma IAPP   K C N T A T C A T Q R L A N F L V H S S N N F G A I L S S T N V G S N T Y
Cat islet IAPP          K C N T A T C A T Q R L A N F L I R S S N N L G A I L Comments to the tables: The sequences given above differ from those given in the priority application at positions 7 and 34 of human IAPP and 7 of feline IAPP. The correct sequence of human IAPP has been published during the priority year (33, 34).

REFERENCES

1. Maclean, N. & Ogilvie, R. F. (1955) Diabetes 4, 367–376.
2. Gepts, W. (1958) Endokrinologie 36, 185–211.
3. Ludwig, G. & Heitner, H. (1967) Z. Inn. Med. 22, 814–818.

4. Westermark, P. & Wilander, E. (1978) Diabetologia 15, 417–421.
5. Yano, B. L. et al (1981) Vet. Pathol. 18, 621–627.
6. Opie, E. L. (1900) J. Exp. Med. 5, 397–428.
7. Westermark, P. (1975) Acta Path. Microbiol. Scand. C 83, 349–446.
8. Eanes, E. D. & Glenner, G. G. (1968) J. Histochem. Cytochem. 16, 673–677.
9. Cornwell, G. G. & Westermark, P. (1980) J. Clin. Path. 33, 1146–1152.
10. Glenner, G. G. (1980) New Engl. J. Med. 302, 1283–1292 & 1333–1343.
11. Glenner, G. G. et al (1971) Science 172, 1150–1151.
12. Benditt, E. P. et al (1971) FEBS Lett. 19, 169–173.
13. Sletten, K. et al (1976) J. Exp. Med. 143, 993–998.
14. Costa, P. P. et al (1978) Proc. Natl. Acad. Sci. U.S.A. 75, 4499–4503.
15. Cohen, D. H. et al (1983) J. Exp. Med. 158, 623–628.
16. Glenner, G. G. & Wong, C. W. (1984) Biochem. Biophys. Res. Commun. 120, 885–890.
17. Gejyo, F. et al (1985) Biochem, Biophys. Res. Commun, 129, 701–705.
18. Pearse, A. G. E. et al (1972) Virchows Arch. Cell. Pathol. 10, 93–107.
19. Westermark, P. et al (1977) Lab. Invest. 37, 212–215.
20. Wide, L. et al Radioimmunoassays and Related Procedures in Medicine, vol. 1 (1978), 143–54.
21. Masters, C. L. et al (1985) EMBO J. 4, 2757–2763.
22. Sternberger, L. A. (1979) Immunocytochemistry. 2nd Edit., John Wiley & Sons, New York.
23. Amara, S. G. et al (1982) Nature 298, 240–244.
24. Rosenfeld, M. G. et al (1983) Nature 304, 129–135.
25. Johnson, K. H. et al (1986) Am. J. Pathol. 125, 416–9.
26. O'Brien, T. D. et al (1985) Am. J. Pathol. 119, 430–5.
27. Johnson, K. H. et al (1985) Vet. Pathol. 22, 463–8.
28. Westermark, P. et al (1983) Diabetologia 24, 342–6.
29. Higuchi, K. et al (1983) Lab. Invest. 48, 231–40.
30. Gambro Lundia AB, EP-A-191, 349.
31. Ciba-Geigy AG, EP-A-206, 302.
32. Westermark, P. et al (1986) Biochem. Biophy. Res. Comm. 140, 827–31.
33. Westermark, P. et al (1987) Proc. Natl. Acad. Sci. U.S.A. 84, 3881–5.
34. Clark, A. et al (1987) Lancet, Aug. 1, 231–4.
35. Westermark, P. et al (1987) Am. J. Pathol. 127, 414–7.
36. Mahoney, W. C. (1985) Analytical Biochemistry 147, 331–335.
37. Uy, R. and Wold, F. (1977) Science 198, 890–896.
38. Tam, J. P. et al (1983) International Journal of Peptide and Protein Research 21, 57–65.
39. Mahoney, W. C., and Hermodson, M. A. (1980) Journal of Biological Chemistry 255, 11199–11203.
40. Edman, P. and Begg, G. (1967) European Journal of Biochemistry 1, 80–91.
41. Mahoney, W. C. et al (1981) Journal of Biological Chemistry 256, 4350–4356.
42. Nute, P. E. and Mahoney, W. C. (1980) Hemoglobin 3, 399–410.

We claim:

1. A polypeptide consisting essentially of: Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn.

2. A polypeptide consisting essentially of: Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly.

3. A polypeptide consisting essentially of: Cys-Ala-Thr-Gln-Arg-Leu-Ala-Asn-Phe-Leu-Ile.

4. A polypeptide consisting essentially of: Lys-Cys-Asn-Thr-Ala-Thr-Cys-Ala-Thr-Gln-Arg-Leu-Ala-Asn-Phe-Leu-Ile-Arg-Ser-Asn-Asn-Leu-Gly-Ala-Ile-Leu.

* * * * *

UNITED STATES PATENT AND TRADEMARK OFFICE
CERTIFICATE OF CORRECTION

PATENT NO. : 5,112,945

DATED : May 12, 1992

INVENTOR(S) : Westermark et al.

It is certified that error appears in the above-identified patent and that said Letters Patent is hereby corrected as shown below:

Title Page

Section [30], "8604270" should read --8604270.2--.

Abstract, line 9, insert a period (--.--) after the word "determined".

Column 2, line 47, "amount" should read --among--.

Column 2, line 50, insert --containing IAPP-- after "complexes".

Column 3, line 14, "<" should read -->--.

Column 3, line 62, insert --be made-- after "may".

Column 7, line 39, "h." should read --hrs.--.

Column 7, line 44, "890DS" should read --890D--.

Column 7, line 52, delete "the" after "for".

Column 9, line 20, "in" should read --is--.

Column 9, line 28, "amyloids" should read --amyloid--.

Column 9, line 43, "is" should read --its--.

UNITED STATES PATENT AND TRADEMARK OFFICE
CERTIFICATE OF CORRECTION

PATENT NO. : 5,112,945

DATED : May 12, 1992

INVENTOR(S) : Westermark et al.

It is certified that error appears in the above-identified patent and that said Letters Patent is hereby corrected as shown below:

Column 9, line 59, "i" should read --in--.

Column 10, lines 28-29, delete "*Not yet determined with certainty.".

Column 10, lines 30-39, "Asp" should be --Asn-- and, therefore, the sequences should read as follows:

--HUMAN IAPP:

10
Lys-Cys-Asn-Thr-Ala-Thr-Cys-Ala-Thr-Gln-Arg-Leu-Ala-Asn-Phe-Leu-Val-His

CAT IAPP:

10
Lys-Cys-Asn-Thr-Ala-Thr-Cys-Ala-Thr-Gln-Arg-Leu-Ala-Asn-Phe-Leu-Ile-Arg
    20                                      30
Ser-Ser-Asn-Asn-Phe-Gly-Ala-Ile-Leu-Ser-Ser-Thr-Asn-Val-Gly-Ser-Asn-Thr-Tyr
        40
Ser-Ser-Asn-Asn-Leu-Gly-Ala-Ile-Leu --

Column 10, line 44, "sequences" should read --sequenced--.

Column 10, line 47, delete "* not yet determined with certainty".

UNITED STATES PATENT AND TRADEMARK OFFICE
CERTIFICATE OF CORRECTION

PATENT NO. : 5,112,945

DATED : May 12, 1992

INVENTOR(S) : Westermark et al.

It is certified that error appears in the above-indentified patent and that said Letters Patent is hereby corrected as shown below:

Column 12, lines 34-36 should read as follows:

--4. A polypeptide consisting essentially of: Lys-Cys-Asn-Thr-Ala-Thr-Cys-Ala-Thr-Gln-Arg-Leu-Ala-Asn-Phe-Leu-Ile-Arg-Ser-Ser-Asn-Asn-Leu-Gly-Ala-Ile-Leu. --

Signed and Sealed this

Fourth Day of January, 1994

BRUCE LEHMAN

*Attest:*

*Attesting Officer*         Commissioner of Patents and Trademarks

UNITED STATES PATENT AND TRADEMARK OFFICE
CERTIFICATE OF CORRECTION

PATENT NO. : 5,112,945
DATED : May 12, 1992
INVENTOR(S) : Westermark et al.

It is certified that error appears in the above-identified patent and that said Letters Patent is hereby corrected as shown below:

Column 12, lines 34-36, a typographical error in the sequence of claim 3 should be corrected to replace the "Ile" with --Val--. Claim 3 should read as follows:

--3. A polypeptide consisting essentially of: Cys-Ala-Thr-Gln-Arg-Leu-Ala-Asn-Phe-Leu-Val.--

Signed and Sealed this

Nineteenth Day of April, 1994

BRUCE LEHMAN

Attest:

Attesting Officer

Commissioner of Patents and Trademarks